United States Patent [19] [11] Patent Number: 4,847,278
Krämer et al. [45] Date of Patent: Jul. 11, 1989

[54] DICHLOROCYCLOPROPYLALKYL-HYDROXYALKYL AZOLE DERIVATIVES

[75] Inventors: Wolfgang Krämer; Karl Steinbeck; Karl H. Büchel, all of Burscheid; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 864,936

[22] Filed: May 20, 1986

[30] Foreign Application Priority Data

May 25, 1985 [DE] Fed. Rep. of Germany ....... 3518916

[51] Int. Cl.⁴ ................. A01N 43/653; C07D 249/12
[52] U.S. Cl. .................................... 514/383; 514/184; 548/101; 548/262; 548/341
[58] Field of Search ................ 548/262, 101; 514/184, 514/383

[56] References Cited

U.S. PATENT DOCUMENTS 4,603,140 7/1986 Reiser et al. .................. 548/341

FOREIGN PATENT DOCUMENTS 0044993 2/1982 European Pat. Off. ............ 548/262
0103798 3/1984 European Pat. Off. ............ 548/262
2535321 4/1984 France ................................. 548/262

Primary Examiner—Glennon H. Hollrah
Assistant Examiner—Patricia L. Morris
Attorney, Agent, or Firm—Sprung Horn Kramer & Woods

[57] ABSTRACT

The novel dichlorocyclopropylalkyl-hydroxyalkyl-azole derivatives of the formula

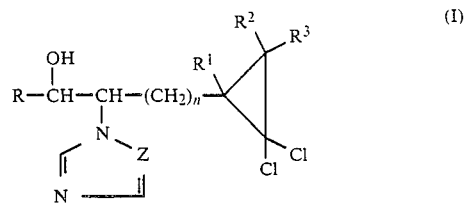

in which
R is optionally substituted cycloalkyl or optionally substituted aryl, or is a grouping of the formula

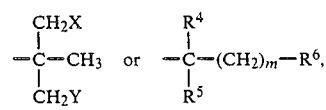

wherein
X is halogen
Y is hydrogen or halogen,
$R^4$ and $R^5$ are identical or different and are alkyl,
$R^6$ is alkyl, halogenoalkyl with more than 2 carbon atoms, alkynyl, alkenyl, optionally substituted cycloalkyl, optionally substituted aryl, optionally substituted aryloxy, optionally substituted arylthio or the grouping

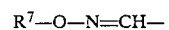

in which
$R^7$ is alkyl, alkenyl or optionally substituted benzyl, and m is the number 0, 1 or 2,
$R^1$, $R^2$ and $R^3$ independently of one another are hydrogen, methyl or chlorine,
n is the number 1 or 2 and
Z is a nitrogen atom or the CH group and their acid addition salts and metal salt complexes are very effective as fungicides.

4 Claims, No Drawings

DICHLOROCYCLOPROPYLALKYL-HYDROXY-ALKYL AZOLE DERIVATIVES

The present invention relates to new dichlorocyclopropylalkyl-hydroxyalkyl-azole derivatives, to fungicidal compositions containing them, and to their use as fungicides.

It has already been disclosed that certain triazolyl-hydroxyalkyl derivatives and triazolyl-ketone derivatives have good fungicidal properties (compare DE-OS (German Published Specification) No. 3,234,627). Thus, for example, 1-cyclopentyl-4,4-dimethyl-2-(1,2,4-triazol-1-yl)-pentan-3-ol, 1-cyclohexyl-4,4-dimethyl-2-(1,2,4-triazol-1-yl)-pentan-3-ol, 4,4-dimethyl-1-(2-methylcyclohexyl)-2-(1,2,4-triazol-1-yl)-pentan-3-ol and 4,4-dimethyl-1-(4-methylcyclohexyl)-2-(1,2,4-triazol-1-yl)-pentan-3-ol and 1-cycloheptyl-4,4-dimethyl-2-(1,2,4-triazol-1-yl)-pentan-3-one can be used for combating fungi. However, the action of these substances is not always completely satisfactory, especially when low amounts are used.

The present invention now provides, as new compounds, the dichlorocyclopropylalkylhydroxyalkyl-azole derivatives of the formula

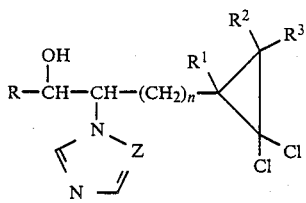

in which

R represents optionally substituted cycloalkyl or optionally substituted aryl, or represents the groupings

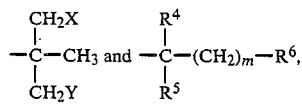

wherein

X represents halogen,

Y represents hydrogen of halogen, $R^4$ and $R^5$ are identical or different and represent alkyl, $R^6$ represents alkyl, halogenoalkyl with more than 2 carbon atoms, alkenyl, alkinyl, optionally substituted cycloalkyl, optionally substituted aryl, optionally substituted aryloxy, optionally substituted arylthio or the grouping

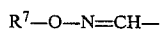

$$R^7-O-N=CH-$$

which $R^7$ represents alkyl, alkenyl or optionally substituted benzyl, and m represents the number 0, 1 or 2, $R^1$, $R^2$ and $R^3$ independently of one another represent hydrogen, methyl or chlorine, n represents the number 1 or 2 and Z represents a nitrogen atom or the CH group, and acid addition salts and metal salt complexes thereof.

The compounds of the formula (I) have several asymmetrically substituted carbon atoms. They can therefore exist in the form of several geometric isomers, which can be obtained in different proportions. In all cases, they are in hhe form of mixtures of optical isomers. The invention relates both to the isomer mixtures and to the individual isomers.

It has furthermore been found that dichlorocyclopropylalkyl-hydroxyalkyl-azole derivatives of the formula (I) and acid addition salts and metal salt complexes thereof are obtained by a process in which azolyl-ketone derivatives of the formula

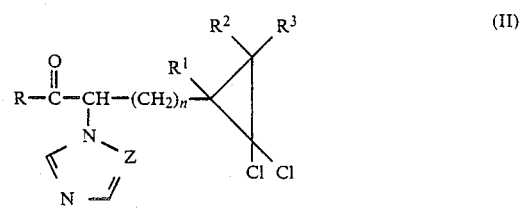

in which

R, $R^1$, $R^2$, $R^3$, n and Z have the abovementioned meanings, are reduced and, if appropriate, an acid or a metal salt is then added on.

Finally, it has been found that the new dichlorocyclopropylalkyl-hydroxyalkyl-azole derivatives of the formula (I) and acid addition salts and metal salt complexes thereof have very good fungicidal properties.

Surprisingly, the substances according to the invention are distinguished by a better fungicidal activity than the triazole derivatives 1-cyclopentyl-4,4-dimethyl-2-(1,2,4-triazol-1-yl)-pentan-3-ol, 1-cyclohexyl-4,4-dimethyl-2-(1,2,4-triazol-1-yl)-pentan-3-ol, 4,4-dimethyl-1-(2-methylcyclohexyl)-2-(1,2,4-triazol-1-yl)-pentan-3-ol, 4,4-dimethyl-1-(4-methylcyclohexyl)-2-(1,2,4-triazol-1-yl)-pentan-3-ol and 1-cycloheptyl-4,4-dimethyl-2-(1,2,4-triazol-1-yl)-pentan-3-one, which are known from the prior art and are closely related compounds structurally and from the point of view of their action.

Formula (I) provides a general definition of the dichlorocyclopropylalkyl-hydroxyalkyl-azole derivatives according to the invention. Preferably, in this formula, R represents cycloalkyl which has 3 to 7 carbon atoms and is optionally substituted by alkyl with 1 to 3 carbon atoms, or represents aryl which has 6 to 10 carbon atoms, it being possible for each of these aryl radicals to be mono-, di- or trisubstituted by identical or different substituents from the group comprising halogen, alkyl with 1 to 4 carbon atoms, alkoxy with 1 to 4 carbon atoms, alkylthio with 1 to 4 carbon atoms, halogenoalkyl with 1 or 2 carbon atoms and 1 to 5 identical or different halogen atoms, such as fluorine and chlorine atoms, halogenoalkoxy with 1 or 2 carbon atoms and 1 to 5 identical or different halogen atoms, such as fluorine or chlorine atoms, halogenoalkylthio with 1 or 2 carbon atoms and 1 to 5 identical or different halogen atoms, such as fluorine or chlorine atoms, nitro, cyano, alkoxycarbonyl with 1 to 4 carbon atoms in the alkoxy part, hydroximinoalkyl with 1 or 2 carbon atoms, alkoximinoalkyl with 1 or 2 carbon atoms in the alkoxy part and 1 or 2 carbon atoms in the alkyl part and phenyl, which can in turn be substituted by halogen and/or alkyl with 1 to 4 carbon atoms, or R represents the groupings

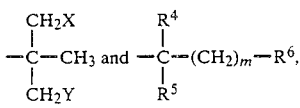

wherein

X preferably represents fluorine or chlorine,

Y preferably represents hydrogen, fluorine or chlorine,

R⁴ preferably represents straight-chain or branched alkyl with 1 to 4 carbon atoms, R⁵ preferably represents straight-chain or branched alkyl with 1 to 4 carbon atoms, R⁶ preferably represents straight-chain or branched alkyl with 1 to 4 carbon atoms, or represents halogenoalkyl with 2 or 3 carbon atoms and 1 to 5 identical or different halogen atoms, such as fluorine and chlorine atoms, or represents alkenyl with 2 to 4 carbon atoms, or represents alkinyl with 2 to 4 carbon atoms, or represents cycloalkyl which has 3 to 7 carbon atoms and is optionally mono-, di- or trisubstituted by identical or different substituents from the group comprising halogen, alkyl with 1 to 4 carbon atoms and/or alkoxy with 1 to 4 carbon atoms, or represents phenyl, phenoxy or phenylthio, it being possible for each of these phenyl radicals to be mono-, di-or trisubstituted by identical or different substituents from the group comprising halogen, alkyl with 1 to 4 carbon atoms, alkoxy with 1 to 4 carbon atoms, alkylthio with 1 to 4 carbon atoms, halogenoalkyl with 1 or 2 carbon atoms and 1 to 5 identical or different halogen atoms, such as fluorine and chlorine atoms, halogenoalkoxy with 1 or 2 carbon atoms and 1 to 5 identical or different halogen atoms, such as fluorine or chlorine atoms, halogenoalkylthio with 1 or 2 carbon atoms and 1 to 5 identical or different halogen atoms, such as fluorine or chlorine atoms, nitro, cyano, alkoxycarbonyl with 1 to 4 carbon atoms in the alkoxy part, hydroximinoalkyl with 1 or 2 carbon atoms, alkoximinoalkyl with 1 or 2 carbon atoms in the alkoxy part and 1 or 2 carbon atoms in the alkyl part and phenyl, which can in turn be substituted by halogen and/or alkyl with 1 to 4 carbon atoms, or R⁶ furthermore represents the grouping

R⁷—O—N=CH— in which

R⁷ preferably represents straight-chain or branched alkyl with 1 to 4 carbon atoms or alkenyl with 2 to 4 carbon atoms, or represents benzyl, which can be mono-, di- or trisubstituted in the phenyl part by identical or different substituents from the group comprising halogen, alkyl with 1 to 4 carbon atoms, alkoxy with 1 to 4 carbon atoms, alkylthio with 1 to 4 carbon atoms, halogenoalkyl with 1 or 2 carbon atoms and 1 to 5 identical or different halogen atoms, such as fluorine and chlorine atoms, halogenoalkoxy with 1 or 2 carbon atoms and 1 to 5 identical or different halogen atoms, such as fluorine or chlorine atoms, halogenoalkylthio with 1 or 2 carbon atoms and 1 to 5 identical or different halogen atoms, such as fluorine or chlorine atoms, nitro, cyano, alkoxycarbonyl with 1 to 4 carbon atoms in the alkoxy part, hydroximinoalkyl with 1 or 2 carbon atoms, alkoximinoalkyl with 1 or 2 carbon atoms in the alkoxy part and 1 or 2 carbon atoms in the alkyl part and phenyl, which can in turn be substituted by halogen and/or alkyl with 1 to 4 carbon atoms, and m represents the number 0, 1 or 2, R¹ represents hydrogen or methyl, R² represents hydrogen, methyl or chlorine, R³ represents hydrogen, methyl or chlorine, n represents the number 1 or 2 and Z represents a nitrogen atom or the CH group.

Particularly preferred compounds of the formula (I) are those in which represents cycloalkyl which has 3 to 6 carbon atoms and is optionally substituted by methyl and/or ethyl, or represents phenyl, which can be mono-, di- or trisubstituted by identical or different substituents from the group comprising fluorine, chlorine, bromine, methyl, ethyl, isopropyl, tert.-butyl, methoxy, methylthio, trifluoromethyl, trifluoromethoxy, trifluoromethylthio, nitro, cyano, methoxycarbonyl, ethoxycarbonyl, hydroximinomethyl, 1-hydroximinoethyl, methoximinomethyl, 1-methoximinoethyl and phenyl, which can in turn be substituted by fluorine, chlorine and/or methyl, or R represents the groupings

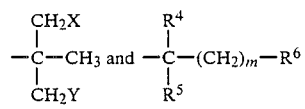

wherein

X represents fluorine or chlorine and

Y represents hydrogen, or

X and Y are identical and represent fluorine or chlorine,

R⁴ represents methyl or ethyl,

R⁵ represents methyl or ethyl,

R⁶ represents methyl, ethyl, isopropyl, vinyl, allyl or propargyl, cyclopentyl which is optionally substituted by chlorine, methyl, ethyl and/or methoxy or cyclohexyl which is optionally substituted by chlorine, methyl, ethyl and/or methoxy, or represents phenyl, phenoxy or phenylthio, it being possible for each of these phenyl radicals to be mono- or disubstituted by identical or different substituents from the group comprising fluorine, chlorine, bromine, methyl, ethyl, isopropyl, tert.-butyl, methoxy, methylthio, trifluoromethyl, trifluoromethoxy, trifluoromethylthio, nitro, cyano, methoxycarbonyl, ethoxycarbonyl, hydroximinomethyl, 1-hydroximinoethyl, methoximinomethyl, 1-methoximinoethyl and phenyl, which can in turn be substituted by fluorine, chlorine and/or methyl or R⁶ furthermore represents the grouping

R⁷—O—N=CH— in which

R⁷ represents methyl, ethyl, propyl, allyl or propargyl, or represents benzyl, which can be mono- or disubstituted in the phenyl part by fluorine, chlorine, bromine, methyl, ethyl, isopropyl, tert. -butyl, methoxy, methylthio, trifluoromethyl, trifluoromethoxy, trifluoromethylthio, nitro, cyano, methoxycarbonyl, ethoxycarbonyl, hydroximinomethyl, 1-hydroximinoethyl, methoximinomethyl, 1-methoximinoethyl or phenyl, which can in turn be substituted by fluorine, chlorine and/or methyl, and m represents the number 0 or 1, $R^1$ represents hydrogen or methyl,
$R^2$ represents hydrogen, methyl or chlorine,
$R^3$ represents hydrogen, methyl or chlorine,
n represents the number 1 or 2 and
Z represents a nitrogen atom.

Other particularly preferred compounds of the formula (I) are those in which
R represents cycloalkyl which has 3 to 6 carbon atoms and is optionally substituted by methyl and/or ethyl, or represents phenyl, which can be mono-, di- or trisubstituted by identical or different substituents from the group comprising fluorine, chlorine, bromine, methyl, ethyl, isopropyl, tert.butyl, methoxy, methylthio, trifluoromethyl, trifluoromethoxy, trifluoromethylthio, nitro, cyano, methoxycarbonyl, ethoxycarbonyl, hydroximinomethyl, 1-hydroximinoethyl, methoximinomethyl, 1-methoximinoethyl and phenyl, which can in turn be substituted by fluorine, chlorine and/or methyl, or R represents the groupings

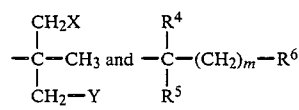

wherein
X represents fluorine or chlorine and
Y represents hydrogen, or
X and Y are identical and represent fluorine or chlorine,
$R^4$ represents methyl or ethyl,
$R^5$ represents methyl or ethyl,
$R^6$ represents methyl, ethyl, isopropyl, vinyl, allyl or propargyl, cyclopentyl which is optionally substituted by chlorine, methyl, ethyl and/or methoxy, or cyclohexyl which is optionally substituted by chlorine, methyl, ethyl and/or methoxy, or represents phenyl, phenoxy or phenylthio, it being possible for each of these phenyl radicals to be mono- or disubstituted by identical or different substituents from the group comprising fluorine, chlorine, bromine, methyl, ethyl, isopropyl, tert.-butyl, methoxy, methylthio, trifluoromethyl, trifluoromethoxy, trifluoromethylthio, nitro, cyano, methoxycarbonyl, ethoxycarbonyl, hydroximinomethyl, 1-hydroximinoethyl, methoximinomethyl, 1-methoximinoethyl and phenyl, which can in turn be substituted by fluorine, chlorine and/or methyl, or
$R^6$ furthermore represents the grouping $R^7$—O—N=CH— in which
$R^7$ represents methyl, ethyl, propyl, allyl or propargyl, or represents benzyl, which can be mono- or disubstituted in the phenyl part by fluorine, chlorine, bromine, methyl, ethyl, isopropyl, tert.-butyl, methoxy, methylthio, trifluoromethyl, trifluoromethoxy, trifluoromethylthio, nitro, cyano, methoxycarbonyl, ethoxycarbonyl, hydroximinomethyl, 1-hydroximinoethyl, methoximinomethyl, 1-methoximinoethyl or phenyl, which can in turn be substituted by fluorine, chlorine and/or methyl, and
m represents the number 0 or 1,
$R^1$ represents hydrogen or methyl,
$R^2$ represents hydrogen, methyl or chlorine,
$R^3$ represents hydrogen, methyl or chlorine,
n represents the number 1 or 2 and
Z represents a CH group.

Addition products of acids and those dichlorocyclopropylalkyl-hydroxyalkyl-azole derivatives of the formula (I) in which R, $R^1$, $R^2$, $R^3$, n and Z have the meanings which have already been mentioned as preferred for these substituents and the index n are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid, 1,5-naphthalenedisulphonic acid and camphorsulphonic acid.

Addition products of salts of metals of main group II to IV and of sub-group I and II and IV to VIII of the periodic table of the elements and of those compounds of the formula (I) in which R, $R^1$, $R^2$, $R^3$, n and Z have the meanings which have already been mentioned as preferred for these substituents and the index n are also preferred compounds according to the invention.

Salts of copper, zinc, manganese magnesium, tin, iron and nickel are particularly preferred here. Possible anions of these salts are those which are derived from acids which lead to physiologically acceptable addition products. Particularly preferred acids of this type in this connection are the hydrogen halide acids, such as, for example, hydrochloric acid and hydrobromic acid, and furthermore phosphoric acid, nitric acid and sulphuric acid.

Examples which may be mentioned of substances according to the invention are those dichlorocyclopropylalkyl-hydroxyalkyl-azole derivatives listed by way of their formulae in the following Table 1.

TABLE 1

| R | Z | n | $R^1$ | $R^2$ | $R^3$ |
|---|---|---|---|---|---|
| CH₃—C(CH₃)(CH₃)— | N | 2 | H | H | H |
| CH₃—C(CH₃)(CH₃)— | " | 2 | " | CH₃ | CH₃ |
| Cl—C₆H₃(Cl)— | " | 2 | " | H | H |
| " | " | " | " | CH₃ | CH₃ |
| Cl—C₆H₄—O—CH₂—C(CH₃)(CH₃)— | N | 2 | H | H | H |

TABLE 1-continued

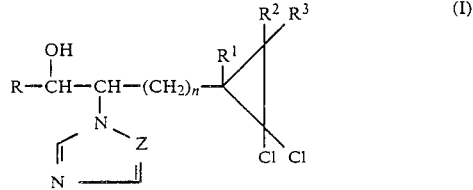

| R | Z | n | $R^1$ | $R^2$ | $R^3$ |
|---|---|---|---|---|---|
| " | " | " | " | $CH_3$ | $CH_3$ |
| " | —CH— | " | " | H | H |
| " | " | " | " | $CH_3$ | $CH_3$ |
| $\begin{array}{c}CH_3\\ \phantom{x}\diagdown\\ CH-C-\\ \phantom{x}\diagup\\ CH_3\end{array}\begin{array}{c}CH_3\\ \\ \\ \\ CH_3\end{array}$ | N | " | " | " | " |
| $Cl-\bigcirc-CH_2-\underset{\underset{CH_3}{\overset{CH_3}{|}}}{C}-$ | " | " | " | H | H |
| " | " | " | " | $CH_3$ | $CH_3$ |
| $CH_2F-\underset{\underset{CH_3}{\overset{CH_3}{|}}}{C}-$ | N | 1 | H | H | H |
| $CH_3-\underset{\underset{CH_3}{\overset{CH_3}{|}}}{C}-$ | " | 1 | $CH_3$ | H | H |
| $CH_3-\underset{\underset{CH_3}{\overset{CH_3}{|}}}{C}-$ | " | " | H | H | $CH_3$ |
| $CH_3-\underset{\underset{CH_3}{\overset{CH_3}{|}}}{C}-$ | " | " | " | Cl | " |

If, for example, 1-(2,2-dichlorocyclopropyl)-4,4-dimethyL-2-(1,2,4-triazol-1-yL)-pentan-3-one is used as the starting substance and sodium borohydride is used as the reducing agent, the course of the process according to the invention can be represented by the following equation:

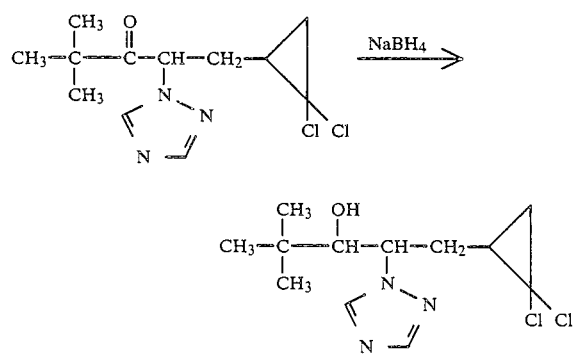

Formula (II) provides a general definition of the azolyl-ketone derivatives required as starting substances in carrying out the process according to the invention. In this formula, R, $R^1$, $R^2$, $R^3$, Z and n preferably have those meanings which have already been mentioned as preferred for these substituents or this index in connection with the description of the substances of the formula (I) according to the invention.

Examples of starting substances of the formula (II) which may be mentioned are those azolyl-ketone derivatives listed by way of their formulae in the following Table 2.

TABLE 2

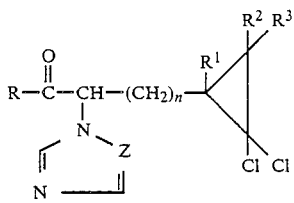

| R | Z | n | $R^1$ | $R^2$ | $R^3$ |
|---|---|---|---|---|---|
| $CH_3-\underset{\underset{CH_3}{\overset{CH_3}{|}}}{C}-$ | N | 2 | H | $CH_3$ | $CH_3$ |
| $Cl-\bigcirc\!\!\!-\!\!Cl$ | N | 2 | H | H | H |
| " | " | " | " | $CH_3$ | $CH_3$ |
| $Cl-\bigcirc-O-CH_2-\underset{\underset{CH_3}{\overset{CH_3}{|}}}{C}-$ | " | " | " | H | H |
| " | " | " | " | $CH_3$ | $CH_3$ |
| " | —CH— | " | " | H | H |
| $Cl-\bigcirc-O-CH_2-\underset{\underset{CH_3}{\overset{CH_3}{|}}}{C}-$ | —CH— | 2 | H | $CH_3$ | $CH_3$ |
| $\begin{array}{c}CH_3\\ \phantom{x}\diagdown\\ CH-C-\\ \phantom{x}\diagup\\ CH_3\end{array}\begin{array}{c}CH_3\\ \\ \\ \\ CH_3\end{array}$ | N | " | " | " | " |
| $Cl-\bigcirc-CH_2-\underset{\underset{CH_3}{\overset{CH_3}{|}}}{C}-$ | N | 2 | H | H | H |
| " | " | " | " | $CH_3$ | $CH_3$ |
| $CH_3-\underset{\underset{CH_3}{\overset{CH_3}{|}}}{C}-$ | " | " | $CH_3$ | " | " |
| " | " | 1 | H | H | " |
| " | " | " | " | Cl | " |

The azolylketone derivatives of the formula (II) have not yet previously been known. They can be prepared by a process in which azolylketones of the formula

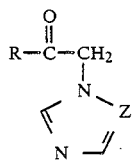

in which

R and Z have the abovementioned meaning, are reacted with compounds of the formula

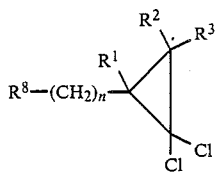

in which $R^1$, $R^2$, $R^3$ and n have the abovementioned meaning and $R^8$ represents an electron-withdrawing leaving group, in the presence of an inert organic diluent, such as, for example, dimethylsulphoxide, and in the presence of an acid-binding agent, such as, for example, potassium hydroxide, at temperatures between 0° C. and 100° C.

The azolylketones of the formula (III) required as starting substances in the above process are known or can be prepared by methods which are known in principle (compare DE-OS (German Published Specification) No. 2,951,163 and DE-OS (German Published Specification) No. 3,048,266). Thus, azolylketones of the formula (III) are obtained, for example, by a process in which halogenoketones of the formula

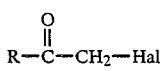

in which

R has the abovementioned meaning and

Hal represents chlorine or bromine, are reacted with 1,2,4-triazole or imidazole in the presence of a diluent, such as, for example, acetone, and in the presence of an acid-binding agent, such as, for example, potassium carbonate, at temperatures between 20° and 150° C.

The halogenketones of the formula (V) can be prepared by a process in which chlorine or bromine is added to ketones of the formula

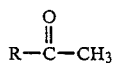

in which

R has the abovementioned meaning, in an inert organic solvent at room temperature; or, for example, the ketones of the formula (VI) are reacted with customary chlorinating agents, such as sulphuryl chloride, at temperatures between 20° and 60° C.

In the abovementioned compounds of the formula (IV), $R^1$, $R^2$, $R^3$ and n preferably have those meanings which have already been mentioned as preferred for these radicals and this index in connection with the description of the substances of the formula (I) according to the invention. $R^8$ preferably represents halogen, such as, for example, chlorine or bromine, or represents p-methyl-phenyl-sulphonyloxy (=tosyl).

The compounds of the formula (IV) are known in some cases (compare Liebigs Ann. Chem. 1979, 920 and Synthesis 1974, 274). The compounds of the formula (IV) which have not yet previously been known can be synthesized by processes which are known in principle. Thus, compounds of the formula (IV) are obtained, for example, by a process in which allyl derivatives of the formula

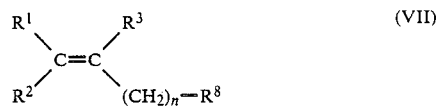

in which $R^1$, $R^2$, $R^3$, $R^8$ and n have the abovementioned meanings, are reacted with chloroform in the presence of triethylbenzylammonium chloride and sodium hydroxide solution at temperatures between 35° and 40° C.

The ketones of the formula (VI) and the allyl derivatives of the formula (VII) are generally known compounds of organic chemistry.

In carrying out the process according to the invention, possible substances for reducing the azolyl-ketone derivatives of the formula (II are all the customary reagents which are suitable for the reduction of such compounds. The reaction is preferably carried out with complex hydrides, if appropriate in the presence of a diluent, or with aluminium isopropylate in the presence of a diluent.

Complex hydrides which can be employed are, preferably, sodium borohydride, calcium borohydride and lithium aluminium hydride.

If the process according to the invention is carried out with complex hydrides, possible diluents are polar organic solvents. Solvents which can preferably be used are alcohols, such as methanol, ethanol, butandl and isopropanol, and furthermore ethers, such as diethyl ether and tetrahydrofuran.

In the reaction with complex hydrides, the reaction temperatures can be varied within a certain range. The reaction is in general carried out at temperatures between −10° C. and +30° C., preferably between 0° C. and +20° C.

In carrying out the reduction according to the invention with complex hydrides, about 1 mole of a complex hydride is employed per mole of azolyl-ketone derivative of the formula (II). The compounds according to the invention are isolated in the customary manner. In general, a procedure is followed in which the reaction mixture is acidified and, if appropriate after prior neutralization, is extracted with an organic solvent of low water-miscibility and the organic phase is then concentrated.

If aluminium isopropylate is used in the process according to the invention, preferred possible diluents are alcohols, such as isopropanol, or inert hydrocarbons, such as benzene.

The reaction temperatures can also be varied within a certain range in the reaction with aluminium isopropylate. In general, the reaction is carried out at temperatures between 20° and 120° C., preferably between 50° and 100° C.

In carrying out the reduction according to the invention with aluminium isopropylate, about 1 to 2 moles of aluminium isopropylate are employed per mole of azolylketone derivative of the formula (II). The compounds according to the invention are isolated in the customary manner.

Possible acids for the preparation of acid addition salts of the compounds of the formula (I) are all those which lead to physiologically acceptable salts. Those acids which have already been mentioned as acids which are preferably to be added on in connection with the description of the substances according to the invention can preferably be used.

The acid addition salts of the compounds of the formula (I) can be prepared in a simple manner by customary salt formation methods. In general, a procedure is followed in which a compound of the formula (I) is dissolved in a suitable inert diluent and an acid is then added. Isolation is effected in a known manner, for example by filtering off the salt and, if appropriate, purifying it by washing with an inert organic solvent.

Salts of those metals which have already been mentioned as metals which are preferably to be added on in connection with the description of the substances according to the invention can preferably be used for the preparation of metal salt complexes of the compounds of the formula (I). Preferred possible anions of these metal salts are hydrogen halide acids, such as, for example, hydrochloric acid and hydrobromic acid, and furthermore phosphoric acid, nitric acid and sulphuric acid.

The metal salt complexes of compounds of the formula (I) can be prepared in a simple manner by customary methods. In general, a procedure is followed in which a metal salt is dissolved in alcohol, such as, for example, ethanol, and a compound of the formula (I) is then added. Isolation is likewise effected in a known manner, for example by filtering off the metal salt complex and if appropriate purifying it by recrystallisation.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as *Xanthomonas oryzae;* Pseudomonas species, such as *Pseudomonas lachrymans;* Erwinia species, such as *Erwinia amylovora;* Pythium species, such as *Pythium ultimum;* Phytophthora species, such as *Phytophthora infestans;* Pseudoperonospora species, such as *Prseudoperonospora humuli* or *Pseudoperonospora cubense;* Plasmopara species, such as *Plasmopara viticola;* Peronospora species, such as *Peronospora pisi* or *P. brassicae;* Erysiphe species, such as *Erysiphe graminis:* Sphaerotheca species, such as *Sphaerotheca fuliginea;* Podosphaera species, such as *Podosphaera leucotricha;* Venturia species, such as *Venturia inaequalis;* Pyrenophora species, such as *Pyrenophoa teres* or *P. graminea;* (conidia form: Drechslera, syn: Helminthosporium); Cochliobolus species, such as *Cochliobolus sativus;* (conidia form: Drechslera, syn: Helminthosporium); Uromyces species, such as *Uromyces appendiculatus;* Puccinia species, such as *Puccinia recondita;* Tilletia species, such as *Tilletia caries;* Ustilago species, such as *Ustilago nuda* or *Ustilago avenae;* Pellicularia species, such as *Pellicularia sasakii;* Pyricularia species, such as *Pyricularia oryzae;* Fusarium species, such as *Fusarium culmorum;* Botrytis species, such as *Botrytis cinerea*; Septoria species such as *Septoria nodorum;* Leptosphaeria species, such as *Leptospharia nodorum;* Cercospora species, such as *Cercospora canescens;* Alternaria species, such as *Alternaria brassicae;* and Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Sphaerotheca species, such as *Sphaerotheca fuligiea* on cucumbers, Venturia species, such as *Venturia inaequalis* on apples, Pyricularia species, such as *Pyricularia oryzae* on rice, and Fusarium species, such as *Fusarium culmorum* on wheat, and also for combating Pyricularia on rice, *Drechslera graminea* and *Pseudocercosporella herpotrichiodes* on cereals. It should be particularly emphasised that the substances according to the invention not only have a protective action but in some cases also have a systemic action. It is thus possible to protect plants from fungal attack if the active compound is fed to the above-ground parts of the plant via the soil and the root or via the seed.

The active compounds according to the invention also have a plant growth-regulating activity.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigatnng coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, aryl sulphonates as well as albumin hydrolysation products; as dispersing agents there are suitable: for example lignin-sulphite waste-liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5% and 90%.

The active compounds according to the invention can be present in the formulations or in the various use forms as a mixture with other known active compounds, such as fungicides, bactericides, insecticides, acaricides, nematicides, herbicides, bird repellants, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomising, misting, vaporising, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The present invention also provides a fungicidal composition containing as active ingredient a compound of the formula (I) according to the present invention in admixture with a solid diluent or carrier or in admixture with a liquid diluent or carrier containing a surface-active agent.

The present invention also provides a method of combating fungi which comprises applying to the fungi, or to a habitat thereof, a compound of the formula (I) according to the present invention alone or in the form of a composition containing as active ingredient a compound of the formula (I) according to the present invention in admixture with a diluent or carrier.

The preparation and use of the substances according to the invention can be seen from the examples which follow.

PREPARATION EXAMPLES

Example 1

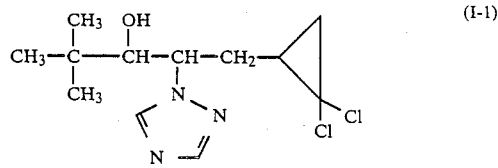

1.9 g (0.047 mole) of sodium borohydride are added in portions to a solution of 13.63 g (0.047 mole) of 1-(2,2-dichlorocyclopropyl)-4,4-dimethyl-2-(1,2,4-triazol-1-yl)-pentan-3-one in 100 ml of methanol at 0° C., with stirring. Thereafter, the mixture is subsequently stirred at room temperature for 4 hours and 20 ml of 5N aqueous hydrochloric acid are then added at 0° C. The reaction mixture is stirred at room temperature for a further 3 hours and then stirred into 100 ml of ice-water. The mixture is extracted twice with 100 ml of methylene chloride each time and the combined organic phases are concentrated under reduced pressure.

13.0 g (95% of theory) of 1-(2,2-dichlorocyclopropyl)-4,4-dimethyl-2-(1,2,4-triazol-1-yl)-pentan-3-ol are obtained as a diastereomer mixture with a refractive index n20D = 1.5007

Preparation of the starting substance

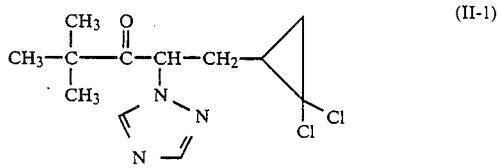

A solution of 8.4 g of potassium hydroxide in 15 ml of water is added to a solution of 25.05 g (0.15 mole) of 1-(1,2,4-triazol-1-yl)-3,3-dimethyl-butan-2-one in 100 ml of dimethylsulphoxide at 0° C., with stirring. 30.5 g (0.15 mole) of 1-bromoethyl-2,2-dichlorocyclopropane are then added dropwise at 20° C., with stirring. The reaction mixture is subsequently stirred at 40° C. for a further 4 hours, poured into 400 ml of ice-water and extracted twice with 100 ml of methylene chloride each time, the combined organic phases are washed three times with 100 ml of water each time and the solvent is stripped off under reduced pressure. 42.1 g of a product are thereby obtained and are dissolved in 100 ml of ethyl acetate. The mixture formed is extracted twice by shaking with 50 ml of 2N aqueous hydrochloric acid each time. The organc phase is concentrated and the residue which remains is taken up in 50 ml of diethyl ether saturated with hydrogen chloride. Thereafter, the solvent is stripped off under reduced pressure and the residue which remains is taken up again in 200 ml of diethyl ether. The solvent is decanted, the residue is taken up in 100 ml of methylene chloride and the mixture is extracted by shaking with saturated aqueous sodium bicarbonate solution (2×100 ml). After the methylene chloride has been distilled off, 14.3 g (32.9% of theory) of 1-(2,2-dichlorocyclopropyl)-4,4-dimethyl-2-(1,2,4-triazol-1-yl)-pentan-3-one is obtained as an oil with a refractive index n20D=1.500.

Example 2

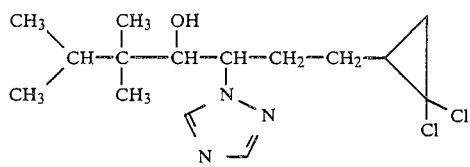 (I-2)

0.27 g (0.007 mole) of sodium borohydride is added in portions to a solution of 2.32 g (0.007 mole) of 1-(2,2-dichlorocyclopropyl)-5,5,6-trimethyl-3-(1,2,4-triazol-1-yl)-heptan-4-one in 30 ml of methanol at 0° C., with stirring. Thereafter, the mixture is subsequently stirred at room temperature for 16 hours and 14 ml of half-concentrated aqueous hydrochloric acid are then added at 0° C. The mixture is stirred at room temperature for 6 hours and then neutralised with aqueous sodium bicarbonate solution.

The mixture is extracted twice with 50 ml of methylene chloride each time and the combined organic phases are concentrated under reduced pressure.

2.3 g (99% of theory) of 1-(2,2-dichlorocyclopropyl)-5,5,6-trimethyl-3-(1,2,4-triazol-1-yl)-heptan-4-ol are obtained as a diastereomer mixture with a refractive index $n_D^{23}$:1.5062.

Preparation of the starting substance

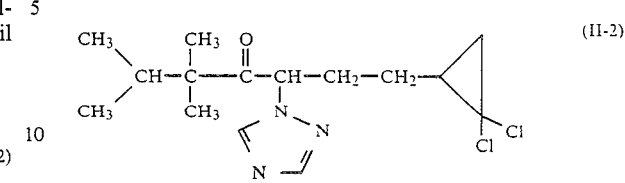 (II-2)

A solution of 1.5 g (0.026 mole) of potassium hydroxide in 1.5 ml of water is added to a solution of 5.04 g (0.026 mole) of 1-(1,2,4-triazol-1-yl)-3,3,4-trimethyl-pentan-2-one and 5.67 g (0.026 mole) of 1-(2-bromoethyl)-2,2-dichlorocyclopropane in 50 ml of dimethylsulphoxide at 0° C., with stirring. The mixture is stirred at room temperature for 16 hours and then poured into 200 ml of water. It is extracted twice with 50 ml of methylene chloride each time and the combined organic phases are washed five times with 50 ml of water each time. The residue which remains after the solvent has been distilled off is subjected to bulb tube distillation.

2.3 g (26.7% of theory) of 1-(2,2-dichlorocyclopropyl)-5,5,6-trimethyl-3-(1,2,4-triazol-1-yl)-heptan-4-one are obtained as an oil of boiling point 150° C. under 0.1 mbar (bulb tube).

The compounds according to the invention listed in the following table are also prepared by the method described in Examples 1 and 2 and the statements contained in the description.

TABLE 3

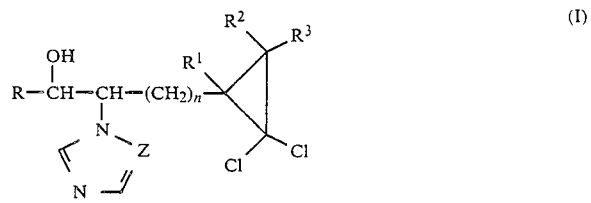 (I)

| Example No. | R | Z | n | R¹ | R² | R³ | Physical constant |
|---|---|---|---|---|---|---|---|
| 3 | H₂C=CH—C(CH₃)₂— | N | 1 | H | CH₃ | CH₃ | $n_D^{20}$ = 1.5040 |
| 4 | (H₃C)₃C— | " | " | " | " | " | M.p. = 115–118° C. |
| 5 | H₂C=CH—C(CH₃)₂— | " | " | " | H | H | $n_D^{20}$ = 1.5083 |
| 6 | Cl—C₆H₄—O—CH₂—C(CH₃)₂— | N | 1 | CH₃ | H | H | amorphous glass |
| 7 | Cl—C₆H₄—O—CH₂—C(CH₃)₂— | " | " | H | CH₃ | CH₃ | M.p. = 151–157° C. |

TABLE 3-continued (I)

$$R-\underset{\underset{\underset{N\diagdown Z}{|}}{\overset{OH}{|}}}{CH}-\underset{\underset{N\diagdown Z}{|}}{CH}-(CH_2)_n-\overset{R^1}{\underset{}{C}}\diagup\overset{R^2}{\underset{Cl}{\overset{R^3}{\diagdown}}}\diagdown Cl$$

| Example No. | R | Z | n | R¹ | R² | R³ | Physical constant |
|---|---|---|---|---|---|---|---|
| 8 | Cl—C₆H₄—O—CH₂—C(CH₃)₂— | " | " | " | H | H | M.p. = 178–188° C. (HCl salt) |
| 9 | H₃C—CH₂—C(CH₃)₂— | " | " | " | " | " | $n_D^{20}$ = 1.4787 |
| 10 | 2,4-Cl₂—C₆H₃—O—CH₂—C(CH₃)₂— | " | " | " | " | " | M.p. = 62–78° C. |
| 11 | CH₃—C(C₂H₅)₂— | " | " | " | " | " | M.p. = 113–116° C. (HCl salt) |
| 12 | (CH₃)₂CH—C(CH₃)₂— | N | 1 | H | H | H | amorphous glass (HCl salt) |

The following starting substances of the formula (II) are obtained by the methods described in Examples 1 and 2:

TABLE 4

(II)

$$R-\underset{\underset{\underset{N\diagdown Z}{|}}{\overset{O}{\|}}}{C}-\underset{\underset{N\diagdown Z}{|}}{CH}-(CH_2)_n-\overset{R^1}{\underset{}{C}}\diagup\overset{R^2}{\underset{Cl}{\overset{R^3}{\diagdown}}}\diagdown Cl$$

| Example No. | R | Z | n | R¹ | R² | R³ | Physical constant |
|---|---|---|---|---|---|---|---|
| 13 | H₂C=CH—C(CH₃)₂— | N | 1 | H | CH₃ | CH₃ | $n_D^{20}$ = 1.5060 |
| 14 | (H₃C)₃C— | " | " | " | " | " | $n_D^{20}$ = 1.4995 |
| 15 | H₂C=CH—C(CH₃)₂— | " | " | " | H | H | $n_D^{20}$ = 1.5056 |
| 16 | Cl—C₆H₄—O—CH₂—C(CH₃)₂— | N | 1 | CH₃ | H | H | $n_D^{20}$ = 1.5327 |

TABLE 4-continued
(II)
| Example No. | R | Z | n | R¹ | R² | R³ | Physical constant |
|---|---|---|---|---|---|---|---|
| 17 | 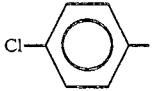 | " | " | H | CH₃ | CH₃ | $n_D^{20} = 1.5291$ |
| 18 | 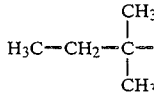 | " | " | " | H | H | amorphous (HCl-salt) |
| 19 | 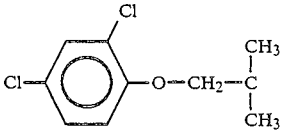 | " | " | " | " | " | $n_D^{20} = 1.5083$ |
| 20 | 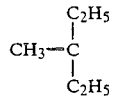 | " | " | " | " | " | viscous oil |
| 21 | 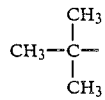 | " | " | " | " | " | $n_D^{20} = 1.4918$ |
| 22 | 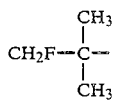 | N | 2 | H | H | H | $Kp_{0.1} = 150°$ C. (bulb-tube) |
| 23 | 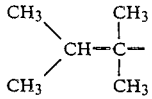 | N | 1 | H | H | H | viscous oil |
| 24 | 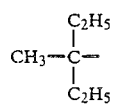 | " | " | " | " | " | viscous oil |
| 25 | 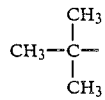 | " | " | " | " | " | $n_D^{20} = 1.5037$ |
The compounds of the formula (I) listed in the following table are prepared by the methods described in Examples 1 and 2.

TABLE 5

$$\text{R—CH(OH)—CH(N\text{-}imidazolyl/triazolyl\text{-}Z)—(CH}_2)_n\text{—}C(R^1)\text{—cyclopropane(R}^2,R^3)(Cl,Cl)} \quad (I)$$

| Example No. | R | Z | n | R¹ | R² | R³ | Physical constant |
|---|---|---|---|---|---|---|---|
| 26 | C₆H₅— (phenyl) | N | 1 | H | H | H | $n_D^{20} = 1.5544$ |
| 27 | Cl—CH=CH—C(CH₃)₂— | N | 1 | H | H | H | $n_D^{20} = 1.5242$ |
| 28 | C₂H₅—O—CH₂—C(CH₃)₂— | N | 1 | H | H | H | $n_D^{20} = 1.4954$ |
| 29 | (CH₃)₂CH—C(CH₃)₂— | N | 1 | H | H | H | (HCl salt) |
| 30 | 4-Cl—C₆H₄— | N | 1 | H | H | H | NMR; CDCl₃ —C[H]—N (imidazolyl) δ = 4.5 Multiplett |
| 31 | 4-Br—C₆H₄—O—CH₂—CH₂—C(CH₃)₂— | N | 1 | H | H | H | M.p. = 155–158° C. (HCl salt) |
| 32 | 4-Cl—C₆H₄—CH₂—C(CH₃)₂— | N | 1 | H | H | H | NMR; CDCl₃ —C[H]—N (imidazolyl) δ = 4.75 Multiple |
| 33 | 4-Cl—C₆H₄—O—CH₂—C(CH₃)₂— | N | 1 | CH₃ | H | H | M.p. = 166–168° C. |
| 34 | H₉C₄—C(CH₃)(C₂H₅)— | N | 1 | H | H | H | $n_D^{20} = 1.4983$ |
| 35 | CH₃—C(CH₂F)₂— | N | 1 | H | H | H | $n_D^{20} = 1.4985$ |
| 36 | 4-Cl—C₆H₄—CH₂—C(CH₃)₂— | N | 2 | H | CH₃ | CH₃ | M.p. = 135–137° C. |

TABLE 5-continued

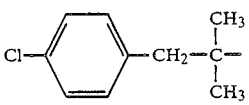

| Example No. | R | Z | n | $R^1$ | $R^2$ | $R^3$ | Physical constant |
|---|---|---|---|---|---|---|---|
| 37 | Cl—C₆H₄—CH₂—C(CH₃)₂— | N | 2 | H | H | H | M.p. = 150–151° C. |

The compounds of the formula (II) listed in the following table 6 are prepared by the methods described in Examples 1 and 2.

TABLE 6

$$\underset{\substack{N\diagdown Z\\N\diagup\diagdown}}{R-\overset{O}{\overset{\|}{C}}-CH-(CH_2)_n-\underset{Cl\ Cl}{\overset{R^2\ R^3}{\overset{R^1}{\triangle}}}} \quad (II)$$

| Example No. | R | Z | n | $R^1$ | $R^2$ | $R^3$ | Physical constant |
|---|---|---|---|---|---|---|---|
| 38 | H₉C₄—C(C₂H₅)(CH₃)— | N | 1 | H | H | H | oil (HCl salt) |
| 39 | Cl—CH=CH—C(CH₃)₂— | N | 1 | H | H | H | $n_D^{20} = 1.5260$ |
| 40 | C₂H₅—O—CH₂—C(CH₃)₂— | N | 1 | H | H | H | $n_D^{20} = 1.4925$ |
| 41 | C₆H₅— | N | 1 | H | H | H | M.p. = 46–48° C. |
| 42 | CH₃—C(CH₂F)₂— | N | 1 | H | H | H | $n_D^{20} = 1.4959$ |

USE EXAMPLES

The substances shown below are employed as comparison compounds in the following use examples:

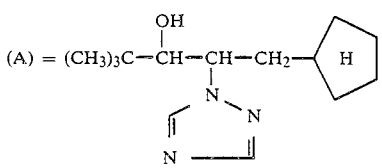

(A) =

-continued

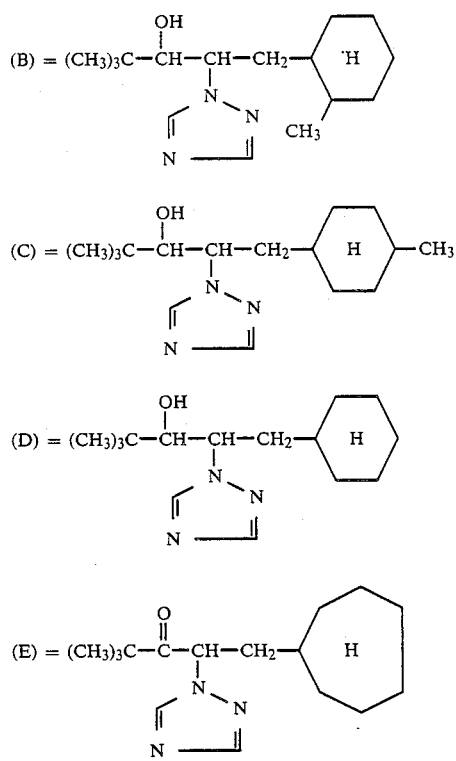

Example A

Sphaerotheca test (cucumber)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a clearly better activity than comparison substance (A) is shown by the substances according to the invention described in examples 1 and 4.

Example B

Sphaerotheca test (cucumber)/systemic Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for systemic properties, standard soil in which young plants ready for testing have been grown is watered with the preparation of active compound. 3 days after the treatment, the plants are dusted with conidia of the fungus Sphaerotheca fuliginea.

The plants are then placed in a greenhouse at 23° to 24° C. and a relative atmospheric humidity of about 75%.

Evaluation is carried out 10 days after the inoculation.

In this test, a clearly better activity than comparison substances (B) and (C) is shown by the substances according to the invention described in examples 1 and 4.

Example C

Venturia test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly better activity than comparison substance (A) is shown by the substances according to the invention described in examples 1 and 4.

Example D

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly better action than comparison substance (D) is shown by the substances according to the invention described in examples 1, 3, 4, 6 and 8.

Example E

Fusarium culmorum test (wheat)/seed treatment

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the wheat are sown 1 cm deep in standard soil and are cultivated in a greenhouse at a temperature of about 18° C. in seedboxes which are exposed to light for 15 hours daily.

About 3 weeks after sowing, the plants are evaluated for symptoms.

In this test, a clearly better action than comparison substance (E) is shown by the substances according to the invention described in examples 3, 4, 25, 27, 28 and 42.

It will be understood that the specification and examples are illustrative, but not limitative of the present invention and that other embodiments within the spirit and scope of the invention will suggest themselves to those skilled in the art.

What is claimed is:

1. A compound of the formula

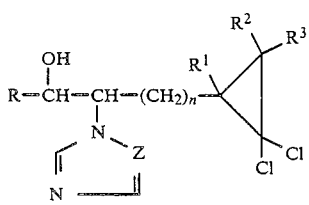

(I)

in which

R is phenyl or mono-substituted phenyl the substituents being identical or different and being selected from the group consisting fluorine and chlorine; or R is a grouping of the formula

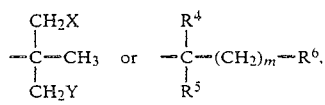

wherein

X is fluorine and
Y is hydrogen or
X and Y are identical and are fluorine
$R^4$ is methyl or ethyl,
$R^5$ is methyl or ethyl,
$R^6$ is ethyl, isopropyl or vinyl or is phenyl, phenoxy, or mono- or disubstituted phenyl, mono- or disubstituted phenoxyl, the substituents, in each case, being identical or different and being selected from the group consisting of fluorine, chlorine and bromine,
m is the number 0, 1 or 2,
$R^1$ is hydrogen or methyl,
$R^2$ is hydrogen or methyl,
$R^3$ is hydrogen or methyl,
n is the number 1 or 2 and
Z is a nitrogen atom, or physiologically acceptable addition product thereof with an acid or salt.

2. A fungicidal composition comprising a fungicidally effective amount of a compound or addition product according to claim 1 in admixture with an inert diluent.

3. A method of combating fungi which comprises administering to such fungi or to a fungus habitat a fungicidally effective amount of a compound or addition product according to claim 1.

4. The method according to claim 3, wherein such compound is, 1-(2,2-dichloro-3,3-dimethyl-cyclopropyl)-4,4-dimethyl-2-(1,2,4-triazol-1-yl)-hex-5-en-3-ol, 1-(2,2-dichloro-1-methyl-cyclopropyl)-4,4-dimethyl-2-(1,2,4-triazol-1-yl)-5-(4-chlorophenoxy)-pentan-3-ol or 1-(2,2-dichloro-cyclopropyl)-4,4-dimethyl-2-(1,2,4-triazol-1-yl)-5-(4-chlorophenoxy)-pentan-3-ol.

* * * * *